(12) United States Patent
Tanino et al.

(10) Patent No.: US 9,518,037 B2
(45) Date of Patent: Dec. 13, 2016

(54) METHOD FOR PRODUCING N,N-DIALKYLHOMOFARNESIC ACID AMIDE

(71) Applicant: Kao Corporation, Tokyo (JP)

(72) Inventors: Kenji Tanino, Wakayama (JP); Takashi Aoki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/436,795

(22) PCT Filed: Oct. 4, 2013

(86) PCT No.: PCT/JP2013/077077
§ 371 (c)(1),
(2) Date: Apr. 17, 2015

(87) PCT Pub. No.: WO2014/061470
PCT Pub. Date: Apr. 24, 2014

(65) Prior Publication Data
US 2016/0168109 A1   Jun. 16, 2016

(30) Foreign Application Priority Data
Oct. 19, 2012 (JP) .................................. 2012-232075

(51) Int. Cl.
*C07D 307/92* (2006.01)
*C07C 231/10* (2006.01)

(52) U.S. Cl.
CPC ........... *C07D 307/92* (2013.01); *C07C 231/10* (2013.01)

(58) Field of Classification Search
CPC ............................ C07D 307/92; C07C 231/10
USPC ........................................................ 549/458
See application file for complete search history.

(56) References Cited

U.S. PATENT DOCUMENTS

2009/0270639 A1* 10/2009 Aoki .................... C07D 307/92
                                                                        549/299
2011/0316040 A1   12/2011 Hirotsuru et al.
2011/0319642 A1   12/2011 Tanino et al.

FOREIGN PATENT DOCUMENTS

| CN | 101490027 A | 7/2009 |
|---|---|---|
| CN | 102317274 A | 1/2012 |
| JP | 2008-56663 A | 3/2008 |
| JP | 2010-189285 A | 9/2010 |
| WO | WO 2010/092972 A1 | 8/2010 |

OTHER PUBLICATIONS

European Patent Office Communication and extended search report issued in the corresponding European Patent Application No. 13847635.3 on Apr. 29, 2016.
"Synthetic perfume Product knowledge and the chemistry", 1996, pp. 380-383 with partial English translation.
Barrero et al., "Synthesis of (±)-Ambrox from (E)-Nerolidol and β-Ionone via Allylic Alcohol [2,3] Sigmatropic Rearrangement", Journal of Organic Chemistry, 1996, vol. 61, pp. 2215-2218.
International Search Report, issued in PCT/JP2013/077077, dated Dec. 17, 2013.
Journal of the American Chemical Society, 1974, vol. 96, No. 17, pp. 5563-5565.
Upar et al., Efficient enantioselective synthesis of (+)-sclareolide and (+)-tetrahydroactinidiolide: chiral LBA-induced biomimetic cyclization, Elsevier, Tetrahedron: Asymmetry, 2009, vol. 20, pp. 1637-1640.

* cited by examiner

*Primary Examiner* — T. Victor Oh
(74) *Attorney, Agent, or Firm* — Birch, Stewart, Kolasch & Birch, LLP

(57) ABSTRACT

Provided are: a method for producing N,N-dialkylhomofarnesic acid amide, which is a precursor of (±)-3a,6,6,9a-tetramethyldodecahydronaphtho[2.1-b]furan that is useful as a fragrance, at a high recovery rate of a raw material, at a high purity and at a high yield; and a method for producing (±)-3a,6,6,9a-tetramethyldodecahydronaphtho[2.1-b]furan. It is a method for producing N,N-dialkylhomofarnesic acid amide, said method including reacting nerolidol with N,N-dialkylformamide dimethyl acetal under the conditions that the N,N-dialkylformamide dimethyl acetal can be refluxed, wherein the molar ratio of the N,N-dialkylformamide dimethyl acetal to the nerolidol is in a range of 1.5 to 3.

20 Claims, No Drawings

METHOD FOR PRODUCING N,N-DIALKYLHOMOFARNESIC ACID AMIDE

TECHNICAL FIELD

The present invention relates to a method for producing N,N-dialkylhomofarnesic acid amide, and a method for producing (±)-3a,6,6,9a-tetramethyldodecahydronaphtho[2.1-b]furan.

BACKGROUND ART (±)-3a,6,6,9a-tetramethyldodecahydronaphtho[2.1-b]furan (hereinafter, referred to as (±)-Ambroxan) is a material of an amber-like fragrance having an excellent aroma property and fragrance retention, and thus it is used as a raw material of a fragrance composition and for perfuming to various products.

[Chemical formula 1]

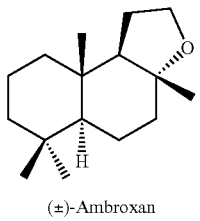

(±)-Ambroxan

Several methods for producing (±)-Ambroxan are known. Recently, methods for producing (±)-Ambroxan through N,N-dialkylhomofarnesic acid amide have been reported. For example, Patent documents 1, 2 and Non-patent document 1 disclose methods for producing (±)-Ambroxan from nerolidol as a starting material through N,N-dimethylhomofarnesic acid amide. As a method for obtaining the N,N-dimethylhomofarnesic acid amide, a method of reacting the nerolidol with N,N-dimethylformamide dimethyl acetal is disclosed.

[Chemical formula 2]

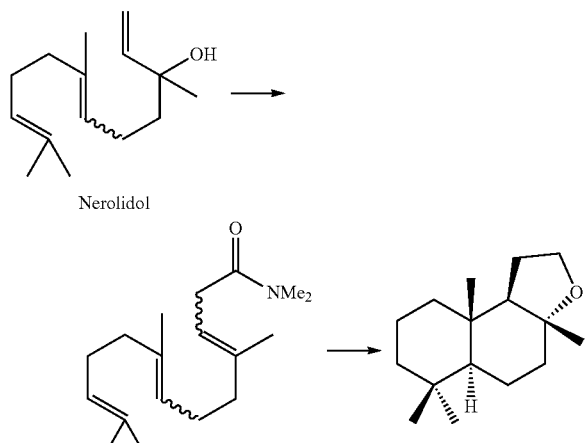

Nerolidol

N,N-dimethylhomofarnesic acid amide (±)-Ambroxan

PRIOR ART DOCUMENTS

Patent Documents

Patent document 1: JP 2008-56663
Patent document 2: JP 2010-189285

Non-Patent Documents

Non-patent document 1: Journal of Organic Chemistry, Vol. 61, p. 2215, 1996

DISCLOSURE OF INVENTION

Problem to be Solved by the Invention

At the time of synthesizing (±)-Ambroxan by any of the methods disclosed in the above-recited Patent documents and the like, for the purpose of obtaining efficiently the (±)-Ambroxan of a high purity at a high yield, it is required to obtain N,N-dialkylhomofarnesic acid amide as the raw material efficiently at a high yield and at a high purity.

However, for obtaining N,N-dialkylhomofarnesic acid amide at a high purity, as mentioned in Non-patent document 1, it is required to add an excessively large amount of expensive N,N-dimethylformamide dimethyl acetal to nerolidol (for example, 840 mol % relative to nerolidol) for causing a reaction. Therefor, a step of separating the resultant reaction product from the large amount of raw material is necessary. Further, since the N,N-dimethylformamide dimethyl acetal is hydrolyzed or polymerized or anything during the reaction, recovery of the N,N-dimethylformamide dimethyl acetal is difficult, rendering the method inefficient.

An object of the present invention is to provide a method for producing N,N-dialkylhomofarnesic acid amide as a precursor of (±)-Ambroxan useful as a fragrance, at a high recovery rate of the raw material, at a high purity and at a high yield; and also to provide a method for producing (±)-3a,6,6,9a-tetramethyldodecahydronaphtho[2.1-b]furan (namely, (±)-Ambroxan).

Means for Solving Problem

The inventors made a study, considering that the factor to impose influences on the recovery rate of the raw material, the purity and the yield is the ratio between nerolidol and N,N-dialkylformamide dimethyl acetal at the time of a reaction. As a result, they found that any of the recovery rate of the raw material, the purity and the yield can be increased by using N,N-dialkylformamide dimethyl acetal at a predetermined ratio to nerolidol in production of N,N-dialkylhomofarnesic acid amide.

That is, the present invention provides the following [1] and [2].

[1] A method for producing N,N-dialkylhomofarnesic acid amide by reacting nerolidol with N,N-dialkylformamide dimethyl acetal under the conditions that the N,N-dialkylformamide dimethyl acetal can be refluxed, wherein the molar ratio of the N,N-dialkylformamide dimethyl acetal to the nerolidol is in a range of 1.5 to 3.

[2] A method for producing (±)-3a,6,6,9a-tetramethyldodecahydronaphtho[2.1-b]furan, comprising Steps 1-4 below:

Step 1: producing N,N-dialkylhomofarnesic acid amide by reacting nerolidol with N,N-dialkylformamide dimethyl acetal under the conditions that the N,N-dialkylformamide dimethyl acetal can be refluxed, wherein the molar ratio of the N,N-dialkylformamide dimethyl acetal to the nerolidol is in a range of 1.5 to 3;

Step 2: cyclizing the N,N-dialkylhomofarnesic acid amide obtained in Step 1 in the presence of an acidic agent and further hydrolyzing to obtain Sclareolide;

Step 3: reducing the Sclareolide obtained in Step 2 so as to obtain Ambroxdiol; and Step 4: dehydrating and cyclizing the Ambroxdiol obtained in Step 3 so as to obtain (±)-3a,6,6,9a-tetramethyldodecahydronaphtho[2.1-b]furan.

Effects of the Invention

According to the present invention, it is possible to provide a method for producing N,N-dialkylhomofarnesic acid amide as a precursor of (±)-3a,6,6,9a-tetramethyldodecahydronaphtho[2.1-b]furan useful as a fragrance, at a high recovery rate of the raw material, at a high purity and at a high yield; and also to provide a method for producing (±)-3a,6,6,9a-tetramethyldodecahydronaphtho[2.1-b]furan.

DESCRIPTION OF THE INVENTION

The method for producing N,N-dialkylhomofarnesic acid amide (hereinafter, represented by Formula (I) below) of the present invention is a method for producing N,N-dialkylhomofarnesic acid amide (I) by reacting nerolidol (hereinafter, represented by Formula (II) below) with N,N-dialkylformamide dimethyl acetal (hereinafter represented by Formula (III) below) under the conditions that the N,N-dialkylformamide dimethyl acetal (III) can be refluxed, wherein the molar ratio of the N,N-dialkylformamide dimethyl acetal (III) to the nerolidol (II) is in a range of 1.5 to 3. It is indicated by Scheme below.

Scheme

[Chemical formula 3]

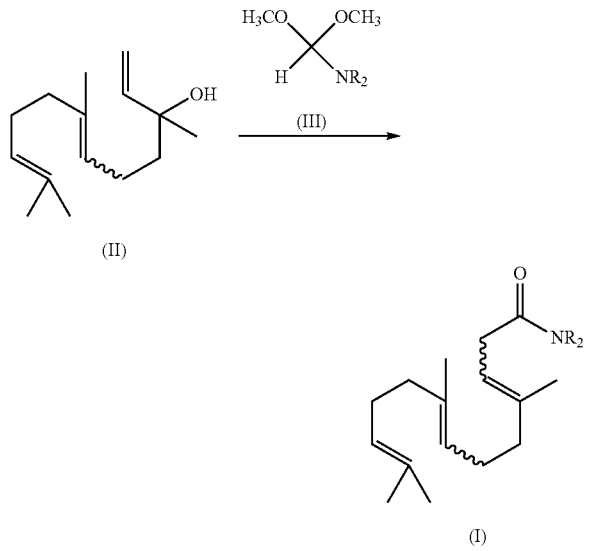

In the above formula, R is an alkyl group, preferably an alkyl group having 1-6 carbon atoms.

Though it is uncertain why N,N-dialkylhomofarnesic acid amide (I) can be obtained at a high recovery rate of the raw material, at a high purity and at a high yield by the producing method of the present invention, the following assumption can be made.

In the present invention, the reaction between the nerolidol (II) and the N,N-dialkylformamide dimethyl acetal (III) is conducted under the conditions that the N,N-dialkylformamide dimethyl acetal can be refluxed. Under the conditions, an amidation reaction of the nerolidol (II) progresses quickly, thereby the intended N,N-dialkylhomofarnesic acid amide (I) can be obtained at a high yield.

Under the conditions, the nerolidol (II) is subjected to an amidation reaction and a self-dehydration reaction. It is considered that, when the N,N-dialkylformamide dimethyl acetal (III) is 1.5 mol times or more, the nerolidol (II) does not evaporate while the amount of N,N-dialkylformamide dimethyl acetal (III) present in the reaction system becomes sufficient, and as a result, the side reaction can be suppressed, the purity is improved remarkably and also the yield is improved.

Meanwhile, under the conditions that the N,N-dialkylformamide dimethyl acetal (III) can be refluxed, the N,N-dialkylformamide dimethyl acetal (III) is subjected gradually to hydrolysis or polymerized by itself. However, by using N,N-dialkylformamide dimethyl acetal (III) of 3 mol times or less relative to the nerolidol, the most part of the N,N-dialkylformamide dimethyl acetal (III) is used for an equilibrium reaction with an intermediate obtained by a reaction with the nerolidol (II), and thus it is considered that formation of the hydrolyzate and the polymers can be decreased remarkably.

[Chemical formula 4]

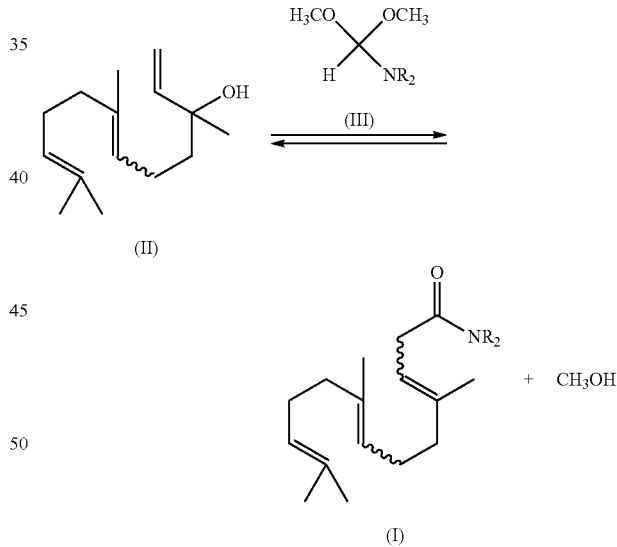

In the above formula, R is an alkyl group.

Hereinafter, the respective components and steps used in the present invention will be explained.

[Nerolidol]

The nerolidol (II) used in the present invention is 3,7,11-trimethyl-1,6,10-dodecatrien-3-ol. Another name of this nerolidol is Peruviol. The nerolidol used in the present invention can be obtained by a method of extracting from Cabreuva oil or a method of synthesizing from linalool through geranylacetone. Further, a commercial product available for the fragrance as Melaleucol from BASF can be used as nerolidol.

[Chemical formula 5]

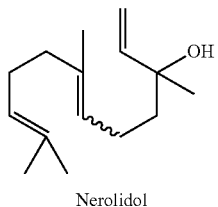

Nerolidol (II)

Nerolidol (II) has geometrical isomers and optical isomers, and in the present invention, any of the isomers and the mixtures can be used favorably.

[N,N-Dialkylformamide Dimethyl Acetal]

N,N-dialkylformamide dimethyl acetal (III) used in the present invention can be obtained by a method of synthesizing from N,N-dialkylformamide and dimethyl sulfate as the raw materials. Alternatively, a commercial product of N,N-dialkylformamide dimethyl acetal (III) may be used directly.

[Chemical formula 6]

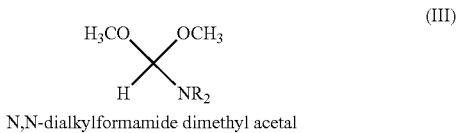

N,N-dialkylformamide dimethyl acetal (III)

In the above formula, R is an alkyl group, preferably an alkyl group having 1-6 carbon atoms. From the viewpoint of the reactivity and from the viewpoint of obtaining N,N-dialkylhomofarnesic acid amide at a high yield, more preferably it is an alkyl group having 1-3 carbon atoms, further preferably it is a methyl group or an ethyl group, and even further preferably, it is a methyl group. For the N,N-dialkylformamide dimethyl acetal (III), N,N-dimethylformamide dimethyl acetal is preferred.

[Method for Producing N,N-Dialkylhomofarnesic Acid Amide (I)]

The method for producing N,N-dialkylhomofarnesic acid amide (I) of the present invention is a method for producing N,N-dialkylhomofarnesic acid amide (I) by reacting nerolidol (II) with N,N-dialkylformamide dimethyl acetal (III) under the conditions that the N,N-dialkylformamide dimethyl acetal (III) can be refluxed, wherein the molar ratio of the N,N-dialkylformamide dimethyl acetal (III) to the nerolidol (II) is in a range of 1.5 to 3.

[Chemical formula 7]

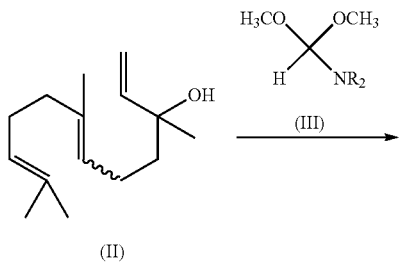

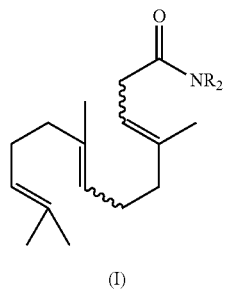

(I)

In the above formula, R is an alkyl group, preferably an alkyl group having 1-6 carbon atoms.

The molar ratio of N,N-dialkylformamide dimethyl acetal (III) to nerolidol (II) is in a range of 1.5 to 3 from the viewpoint of increasing the recovery rate of the raw material (N,N-dialkylformamide dimethyl acetal (III)) and obtaining the intended N,N-dialkylhomofarnesic acid amide (I) at a high purity and at a high yield. The molar ratio of N,N-dialkylformamide dimethyl acetal (III) to nerolidol (II) is preferably in a range of 1.7 to 3, more preferably 2 to 3, and further preferably 2 to 2.5 from the viewpoint of obtaining an intended N,N-dialkylhomofarnesic acid amide (I) at a high purity and at a high yield.

Further, from the viewpoint of increasing the recovery rate of the raw material, the molar ratio of N,N-dialkylformamide dimethyl acetal (III) to nerolidol (II) is preferably in a range of 1.7 to 3, more preferably 2 to 3, and further preferably 2 to 2.5.

N,N-dialkylformamide dimethyl acetal that has not been reacted or recovered is decomposed by hydrolysis so as to form N,N-dialkylformamide. The N,N-dialkylformamide, in particular N,N-dimethylformamide, has an amine-like odor, and thus, N,N-dialkylformamide remaining in the N,N-dialkylhomofarnesic acid amide (I) as a product applies an unpleasant odor to the fragrance as a final product, or it results in increase in the load of a purification for removing the residue or in deterioration in the yield. To avoid such problems, it is preferable that the amount of the residue of the decomposition product is decreased.

From the viewpoint of decreasing the amount of residue of the decomposition product of N,N-dialkylformamide dimethyl acetal, the molar ratio of the N,N-dialkylformamide dimethyl acetal (III) to the nerolidol (II) is preferably in a range of 1.5 to 2.5, more preferably 1.5 to 2, and further preferably 1.75 to 2.

(Reaction Conditions)

The present invention is carried out under the conditions that N,N-dialkylformamide dimethyl acetal (III) can be refluxed. The conditions that the N,N-dialkylformamide dimethyl acetal (III) can be refluxed are that the temperature is equal to or higher than the boiling point of the N,N-dialkylformamide dimethyl acetal (III) under the conditions of atmospheric pressure, namely a pressure of 101 kPa. From the viewpoint of reactivity, the conditions that the N,N-dialkylformamide dimethyl acetal (III) can be refluxed are preferably that the temperature is 100° C. or higher. From the viewpoint of separating efficiently an alcohol obtained as a by-product and the N,N-dialkylformamide dimethyl acetal (III) as the raw material in a case of using a rectifier, the conditions that the N,N-dialkylformamide dimethyl acetal (III) can be refluxed are that the temperature is in a range of more preferably 100 to 200° C., and further preferably, 100 to 150° C.

The present invention can be carried out under the atmospheric pressure, a pressure slightly higher than the atmospheric pressure, or a pressure slightly lower than the atmospheric pressure.

(Organic Solvent)

In the present invention, at the time of reaction under the conditions that the N,N-dialkylformamide dimethyl acetal (III) can be refluxed, an organic solvent may be included or not.

For the organic solvent, from the viewpoint of avoiding influences on the solubility and the reaction of the raw material and the product, hydrocarbons are preferred. From the viewpoint of keeping the reaction temperature within a favorable range, toluene and xylene are preferred, and xylene is preferred further.

From the viewpoint of improving the purity and the yield of the product, the use amount of the organic solvent is preferably less than 1000 mass % relative to the nerolidol (II), more preferably less than 100 mass %, and further preferably, no organic solvent is contained.

(Rectification)

In the present invention, at the time of reaction under the conditions that the N,N-dialkylformamide dimethyl acetal (III) can be refluxed, it is preferable that the reaction is conducted while separating an alcohol obtained as a by-product and the N,N-dialkylformamide dimethyl acetal (III) as the raw material by use of a rectifier.

Namely, by use of the rectifier, the alcohol obtained as a by-product is removed to the outside of the system efficiently while maintaining the conditions that the N,N-dialkylformamide dimethyl acetal (III) can be refluxed. Thereby, the effect of the present invention is enhanced further.

From the viewpoint of the separation capability, it is preferable that the number of plates of the rectifier in use is increased. Preferably, the number of the plates is 3 or more, and more preferably, 5 or more. From the viewpoint of reaction efficiency and the load of facilities, it is preferable that the number of plates is decreased. Preferably, the number of plates is 40 or less, more preferably 30 or less, and further preferably 10 or less. From the above-mentioned viewpoints, the number of plates of the rectifier in use is preferably 3 or more, more preferably in a range of 3 to 40, and further preferably 5 to 30.

From the viewpoint of progressing the reaction promptly and increasing the purity of the resultant N,N-dialkylhomofarnesic acid amide (I), preferably, the reflux ratio is 3 or more, more preferably 5 or more, further preferably 8 or more, even further preferably 9 or more, and even further preferably 10 or more. In the present invention, a reflux ratio is a ratio between an amount of a liquid returning from a condenser to the inside of the system and an amount of the liquid discharged to the outside of the system.

From the viewpoint of the efficiency of reaction, the yield and the purity of the product, the recovery rate of the raw material and suppression of decomposition products, a lower reflux ratio is preferred in the present invention. Preferably, it is 40 or less, more preferably 30 or less, further preferably 25 or less, even further preferably 20 or less, and even further preferably 15 or less. Taking these viewpoints together, the reflux ratio in the present invention is preferably in a range of 3 to 40, more preferably 5 to 30, further preferably 8 to 25, even further preferably 9 to 20, and even further preferably 10 to 15.

[Method for Producing (±)-3a,6,6,9a-tetramethyldodecahydronaphtho[2.1-b]furan]

By using the N,N-dialkylhomofarnesic acid amide (I) of a high purity obtained according to the present invention, it is possible to obtain efficiently (±)-3a,6,6,9a-tetramethyldodecahydronaphtho[2.1-b]furan (VI), namely, (±)-Ambroxan of a high quality.

Though examples of the method for producing (±)-Ambroxan (VI) using N,N-dialkylhomofarnesic acid amide (I) include the methods as mentioned in the above-recited documents, the method below is preferably applied.

That is, it is preferable that the method includes Steps 1-4 below.

Step 1: a step of producing N,N-dialkylhomofarnesic acid amide (I) by reacting nerolidol (II) with N,N-dialkylformamide dimethyl acetal (III) under the conditions that the N,N-dialkylformamide dimethyl acetal (III) can be refluxed, wherein the molar ratio of the N,N-dialkylformamide dimethyl acetal (III) to the nerolidol (II) is in a range of 1.5 to 3;

Step 2: a step of cyclizing the N,N-dialkylhomofarnesic acid amide (I) obtained in Step 1 in the presence of an acidic agent, and further hydrolyzing to obtain Sclareolide (IV);

Step 3: a step of reducing the Sclareolide (IV) obtained in Step 2 so as to obtain Ambroxdiol (V); and Step 4: a step of dehydrating and cyclizing the Ambroxdiol (V) obtained in Step 3 so as to obtain (±)-3a,6,6,9a-tetramethyldodecahydronaphtho[2.1-b]furan (namely, (±)-Ambroxan) (VI).

[Chemical formula 8]

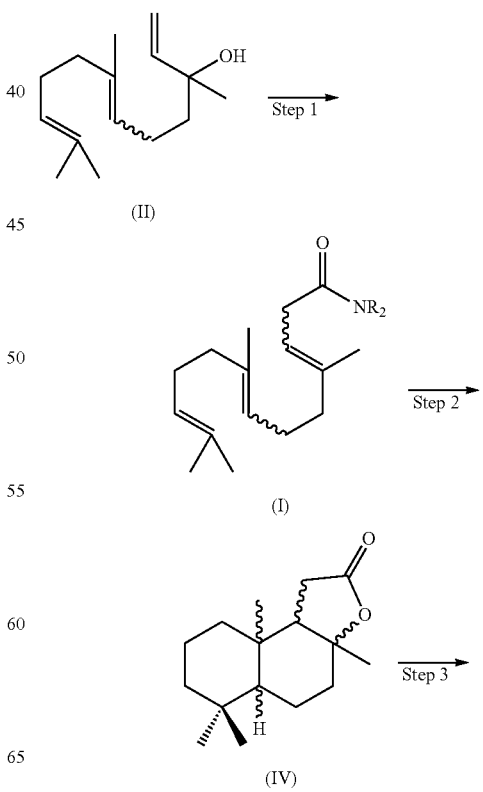

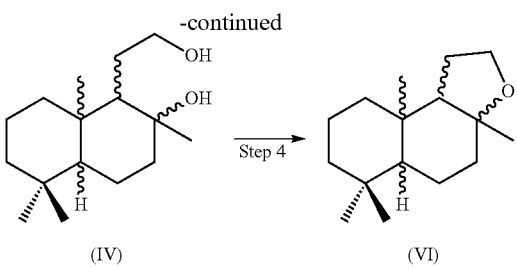

(IV)          (VI)

In the Chemical formula, R is an alkyl group, preferably an alkyl group having 1-6 carbon atoms.

(Step 1)

Step 1 is similar to the above-mentioned method for producing the N,N-dialkylhomofarnesic acid amide (I), and the preferable aspect and range are the same as the above-mentioned ones.

(Step 2)

Step 2 is a step of cyclizing the N,N-dialkylhomofarnesic acid amide (I) obtained in Step 1 in the presence of an acidic agent and further hydrolyzing to obtain Sclareolide (IV).

[Chemical formula 9]

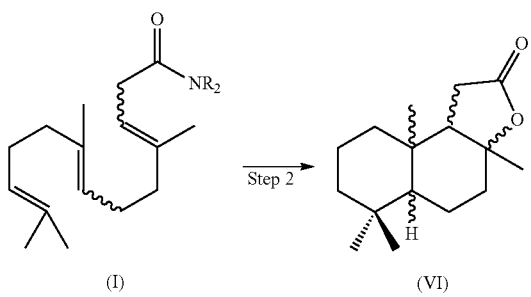

(I)          (VI)

In this step, first, N,N-dialkylhomofarnesic acid amide (I) is dropped into a mixed liquid of the acidic agent and a solvent so as to conduct a cyclization reaction, thereby obtaining a cyclic enamine derivative.

Examples of the acidic agent used in the cyclization reaction include sulfuric acid or Brönsted acid having an acid strength equal to or higher than an acid strength of sulfuric acid, such as methanesulfonic acid, paratoluenesulfonic acid, chlorosulfonic acid, and trifluoromethane sulfonic acid, and Lewis acids such as a metal chloride and a boron trifluoride ether complex. From the viewpoint of diastereofacial selectivity of the Sclareolide (IV) and also from the viewpoint of cost reduction and easy handling, the acidic agent is preferably sulfuric acid, methanesulfonic acid, chlorosulfonic acid, tin tetrachloride, or titanium tetrachloride.

It is preferable that the acidic agent is used in an amount of 0.1 to 10 mol times relative to N,N-dialkylhomofarnesic acid amide (I). From the viewpoint of converting the raw material completely, it is preferable that the acidic agent is used in an amount of 2 mol times or more relative to the N,N-dialkylhomofarnesic acid amide (I). From the viewpoint of production cost and the load of post treatment, the preferred amount is 7 mol times or less relative to the N,N-dialkylhomofarnesic acid amide (I).

From the viewpoint of suppressing the yield degradation caused by a polymerization of the raw material, it is preferable that in the cyclization reaction, a solvent of 1 to 100 mass times relative to N,N-dialkylhomofarnesic acid amide (I) is used. Applicable solvent is not limited in particular as long as it is inactive in the presence of acidic acid, and the examples include hydrocarbons, halogenated hydrocarbons, nitrohydrocarbons and ethers. From the viewpoint of recovery operation, a water-insoluble solvent having a low boiling point is preferred. Dichloromethane, chloroform, toluene, xylene and the like are preferred further as they are inexpensive.

Regarding N,N-dialkylhomofarnesic acid amide (I), it is preferable to drop a solution of any of these solvents or the N,N-dialkylhomofarnesic acid amide (I) directly. From the viewpoint of productivity, it is more preferable to drop the N,N-dialkylhomofarnesic acid amide (I) directly without using a solvent.

The cyclization reaction can be performed at a temperature in a range of −70 to 100° C. From the viewpoint of equipment load in case of industrialization, it is preferable that the reaction is performed at a temperature of −20° C. or higher. Further, from the viewpoint of suppressing a side reaction such as polymerization, it is preferable that the cyclization reaction is conducted at a temperature of 50° C. or lower, and from the viewpoint of obtaining (±)-Sclareolide highly-selectively, it is more preferable that the cyclization reaction is conducted at a temperature of 10° C. or lower.

After completion of dropping of the N,N-dialkylhomofarnesic acid amide (I), water is added, then it is preferable that the reaction mixture is stirred at a temperature in a range from 0° C. to the boiling point of the solvent while keeping the acidic condition by the time of confirming disappearance of the cyclic enamine derivative as an intermediate.

After completion of the hydrolysis, the acidic agent in the reaction mixture is neutralized, which is followed by operations for extraction with an organic solvent and removal of the solvent, thereby Sclareolide (IV) is obtained.

(Step 3)

Step 3 is a step of reducing the Sclareolide (IV) obtained in Step 2 so as to obtain Ambroxdiol (V).

[Chemical formula 10]

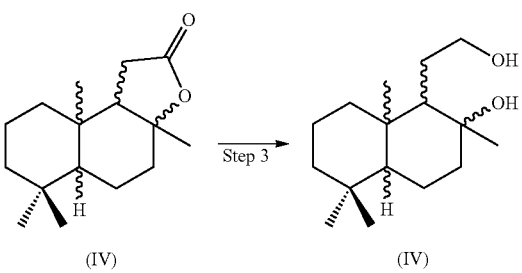

(IV)          (IV)

It is preferable that the reduction reaction of this step is conducted in the presence of a reducer such as lithium aluminum hydride.

(Step 4)

Step 4 is a step of dehydrating and cyclizing the Ambroxdiol (V) obtained in Step 3 so as to obtain (±)-3a,6,6,9a-tetramethyldodecahydronaphtho[2.1-b]furan (namely, (±)-Ambroxan) (VI).

[Chemical formula 11]

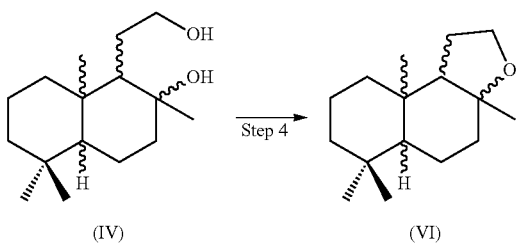

It is preferable to use a dehydrating agent such as phosphorus oxychloride for the dehydration-cyclization.

As a result of conducting the above-mentioned steps, (±)-Ambroxan (VI) of a high quality can be obtained efficiently.

With regard to the above-described embodiments, the present invention further discloses a method for producing N,N-dialkylhomofarnesic acid amide and a method for producing (±)-3a,6,6,9a-tetramethyldodecahydronaphtho[2.1-b]furan.

<1> A method for producing N,N-dialkylhomofarnesic acid amide by reacting nerolidol with N,N-dialkylformamide dimethyl acetal under the condition that the N,N-dialkylformamide dimethyl acetal can be refluxed, wherein the molar ratio of the N,N-dialkylformamide dimethyl acetal to the nerolidol is in a range of 1.5 to 3.

<2> The method for producing N,N-dialkylhomofarnesic acid amide according to <1>, wherein the N,N-dialkylformamide dimethyl acetal is represented by Formula (III) below.

[Chemical formula 12]

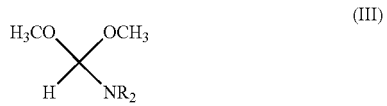

In the above formula, R is an alkyl group, preferably an alkyl group having 1-6 carbon atoms, more preferably an alkyl group having 1-3 carbon atoms, further preferably a methyl group or an ethyl group, and even further preferably a methyl group.

<3> The method for producing N,N-dialkylhomofarnesic acid amide according to <1> or <2>, wherein the molar ratio of the N,N-dialkylformamide dimethyl acetal to the nerolidol is in a range of preferably 1.7 to 3, more preferably 2 to 3, and further preferably 2 to 2.5.

<4> The method for producing N,N-dialkylhomofarnesic acid amide according to any one of <1> to <3>, wherein the reaction is conducted under the conditions that the N,N-dialkylformamide dimethyl acetal can be refluxed in a case where no organic solvent is contained or an organic solvent is contained in an amount of less than 100 mass %, preferably in an amount of less than 100 mass % relative to the nerolidol.

<5> The method for producing N,N-dialkylhomofarnesic acid amide according to <4>, wherein the organic solvent is a hydrocarbon, preferably toluene or xylene, and more preferably xylene.

<6> The method for producing N,N-dialkylhomofarnesic acid amide according to any one of <1> to <5>, wherein the reflux is conducted under the conditions that the reflux ratio is 3 or more, preferably 5 or more, more preferably 8 or more, further preferably 9 or more, even further preferably 10 or more; 40 or less, preferably 30 or less, more preferably 25 or less, further preferably 20 or less, and even further preferably 15 or less.

<7> The method for producing N,N-dialkylhomofarnesic acid amide according to any one of <1> to <6>, wherein the reflux is conducted using a rectifier.

<8> The method for producing N,N-dialkylhomofarnesic acid amide according to <7>, wherein the number of plates of the rectifier is 3 or more, and preferably 5 or more; 40 or less, preferably 30 or less, and more preferably 10 or less.

<9> The method for producing N,N-dialkylhomofarnesic acid amide according to any one of <1> to <6>, wherein the conditions that the N,N-dialkylformamide dimethyl acetal is refluxed is that the temperature is equal to or higher than the boiling point of the N,N-dialkylformamide dimethyl acetal (III), and preferably 100° C. or higher, under the conditions of atmospheric pressure, namely, under the pressure of 101 kPa.

<10> The method for producing N,N-dialkylhomofarnesic acid amide according to <7> or <8>, wherein the temperature as the conditions that the N,N-dialkylformamide dimethyl acetal can be refluxed is in a range of 100 to 200° C., preferably 100 to 150° C.

<11> A method for producing (±)-3a,6,6,9a-tetramethyldodecahydronaphtho[2.1-b]furan, comprising Steps 1-4 below:

Step 1: reacting nerolidol with N,N-dialkylformamide dimethyl acetal under the conditions that the N,N-dialkylformamide dimethyl acetal can be refluxed to produce N,N-dialkylhomofarnesic acid amide, wherein the molar ratio of the N,N-dialkylformamide dimethyl acetal to the nerolidol is in a range of 1.5 to 3;

Step 2: cyclizing the N,N-dialkylhomofarnesic acid amide obtained in Step 1 in the presence of an acidic agent and further hydrolyzing to obtain Sclareolide;

Step 3: reducing the Sclareolide obtained in Step 2 so as to obtain Ambroxdiol; and Step 4: dehydrating and cyclizing the Ambroxdiol obtained in Step 3 so as to obtain (±)-3a,6,6,9a-tetramethyldodecahydronaphtho[2.1-b]furan.

<12> The method for producing (±)-3a,6,6,9a-tetramethyldodecahydronaphtho[2.1-b]furan according to <11>, wherein the N,N-dialkylformamide dimethyl acetal is represented by the following Formula (III).

[Chemical formula 13]

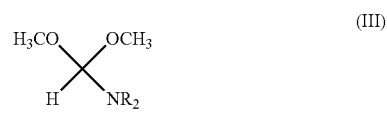

In the above formula, R is an alkyl group, preferably an alkyl group having 1-6 carbon atoms.

<13> The method for producing (±)-3a,6,6,9a-tetramethyldodecahydronaphtho[2.1-b]furan according to <11> or <12>, wherein the acidic agent is sulfuric acid or Brönsted acid having an acid strength equal to or higher than an acid strength of sulfuric acid, such as methanesulfonic acid, paratoluenesulfonic acid, chlorosulfonic acid and trifluoromethane sulfonic acid, and Lewis acids such as a metal chloride and a boron trifluoride ether complex; preferably, sulfuric acid, methanesulfonic acid, chlorosulfonic acid, tin tetrachloride, or titanium tetrachloride.

<14> The method for producing (±)-3a,6,6,9a-tetramethyldodecahydronaphtho[2.1-b]furan according to any one of <11> to <13>, wherein the acidic agent is used in an amount of 0.1 to 10 mol times, preferably 2 mol times or more, and preferably 7 mol times or less relative to N,N-dialkylhomofarnesic acid amide (I).

<15> The method for producing (±)-3a,6,6,9a-tetramethyldodecahydronaphtho[2.1-b]furan according to any one of <11> to <14>, wherein a solvent is used further in an amount of 1 to 100 mass times relative to the N,N-dialkylhomofarnesic acid amide (I) in Step 2.

<16> The method for producing (±)-3a,6,6,9a-tetramethyldodecahydronaphtho[2.1-b]furan according to <15>, wherein the solvent is a hydrocarbon, a halogenated hydrocarbon, a nitrohydrocarbon, or an ether; preferably, dichloromethane, chloroform, toluene or xylene.

<17> The method for producing (±)-3a,6,6,9a-tetramethyldodecahydronaphtho[2.1-b]furan according to any one of <11> to <16>, wherein the cyclization reaction in Step 2 is conducted at a temperature in a range of −70° C. to 100° C., preferably at −20° C. or higher; preferably at 50° C. or lower, and more preferably at 10° C. or lower.

<18> The method for producing (±)-3a,6,6,9a-tetramethyldodecahydronaphtho[2.1-b]furan according to any one of <11> to <17>, wherein the reduction in Step 3 is conducted in the presence of a reducer, preferably in the presence of lithium aluminum hydride.

<19> The method for producing (±)-3a,6,6,9a-tetramethyldodecahydronaphtho[2.1-b]furan according to any one of <11> to <17>, wherein the dehydration-cyclization in Step 4 is conducted by using a dehydrating agent, preferably by using phosphorus oxychloride.

EXAMPLES

Quantification of Yield, Purity, and Recovery Rate of Raw Material DMF-DMA

The yield, the purity and the recovery rate of raw material DMF-DMA were measured by gas chromatography (hereinafter, referred to as GC) under the following GC analytical conditions, and represented as mol % relative to nerolidol used as the raw material. Regarding the yield, a GC internal standard analytical method was used by applying a calibration curve of N,N-dimethylhomofarnesic acid amide. For quantitative analyses of (±)-Sclareolide (IV), (±)-Ambroxdiol (V) and (±)-Ambroxan (VI), respective calibration curves for (±)-Sclareolide (IV), (±)-Ambroxdiol (V) and (±)-Ambroxan (VI) were used.

For the yield and the purity, greater numeric values are favorable.

The recovery rate of the raw material DMF-DMA is a value obtained by dividing the total molar amount of the N,N-dimethylhomofarnesic acid amide after reaction and the recovered N,N-dimethylformamide dimethyl acetal by the molar amount of N,N-dimethylformamide dimethyl acetal before reaction.

For the recovery rate of the raw material DMF-DMA, a greater numeric value is favorable.

[Decomposition Amount of Raw Material DMF-DMA]

Decomposition amount of the raw material DMF-DMA (mol % relative to nerolidol used as a raw material) is a value of the difference obtained by subtracting an amount of reacted DMF-DMA (mol % relative to nerolidol used as a raw material) and an amount of recovered DMF-DMA (mol % relative to nerolidol used as a raw material) from an amount of charged DMF-DMA (mol % relative to nerolidol used as a raw material), and a smaller value is favorable.

(GC Analytical Conditions)
GC analyzing equipment: Agilent Technology 6850A (trade name, manufactured by Agilent Technologies)
Column: DB-WAX (trade name, manufactured by Agilent Technologies, 30 m×250 μm×0.25 μm)
Temperature program: 80° C.→6° C./min.→220° C. in an oven (held for 32 minutes) (55 minutes in total)
Carrier gas: helium
Flow rate: 2.0 ml/min.
Inlet: 200° C.
Injection volume: 1 μm (split 100:1)
Detector: FID 280° C.
Internal standard: n-tetradecane Example 1

In accordance with the following Scheme, nerolidol (II) and N,N-dimethylformamide dimethyl acetal (III-1) were reacted with each other to obtain N,N-dimethylhomofarnesic acid amide (I-1).

Scheme

[Chemical formula 14]

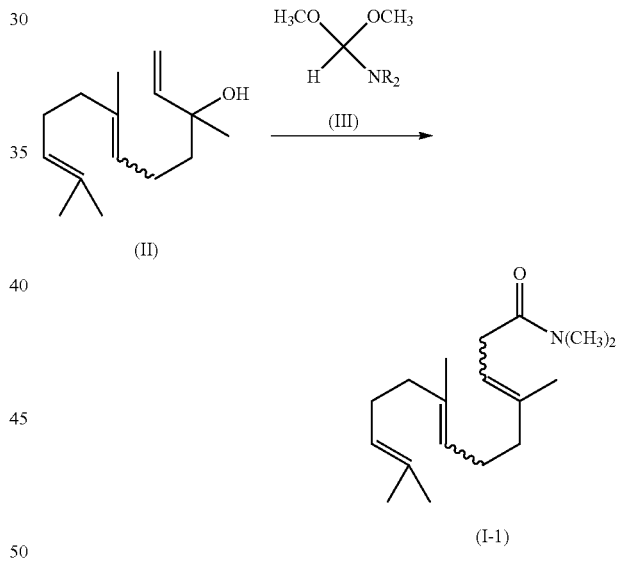

Into a reaction device equipped with a 5-plate rectifier, 120.0 g of xylene (923 mass % relative to nerolidol), 13.0 g of nerolidol (II) (purity: 98.6%, pure content: 12.8 g, 57.7 mmol) and 14.6 g of N,N-dimethylformamide dimethyl acetal (III-1) (purity: 94.0%, pure content: 13.7 g, 115.3 mmol; 200 mol % relative to nerolidol) were introduced and heated to reach a temperature in a range of 120 to 130° C. under an atmospheric pressure. It was stirred for 55 hours while the reflux ratio was set to 10, methanol as a by-product was separated while being distilled, and N,N-dimethylformamide dimethyl acetal was allowed to return to the reaction system.

Under a reduced pressure, the xylene and the N,N-dimethylformamide dimethyl acetal (III-1) were distilled, so that 15.5 g of N,N-dimethylhomofarnesic acid amide (I-1) (purity: 83.9%, pure content: 13.0 g, 47.0 mmol, yield:

81.5%) was obtained. The pure content of the N,N-dimethylformamide dimethyl acetal (III-1) recovered together with methanol and xylene was 6.9 g (58.1 mmol). The recovery rate of N,N-dimethylformamide dimethyl acetal (III-1) was 81.5%, and the decomposition amount of the N,N-dimethylformamide dimethyl acetal was 37.0%.

Examples 2-4 and Comparative Examples 1-2

N,N-dimethylhomofarnesic acid amide (I-1) was obtained similarly to Example 1 except that the amount (in terms of pure content) of the N,N-dimethylformamide dimethyl acetal (III-1) was changed as illustrated in Table 1. Table 1 illustrates the purity and the yield of the resultant N,N-dimethylhomofarnesic acid amide (I-1), and the recovery rate of N,N-dimethylformamide dimethyl acetal (III-1) and the decomposition amount of N,N-dimethylformamide dimethyl acetal.

It is evident from Table 1 and Table 2 that according to the producing methods in the Examples, the purity of the resultant N,N-dimethylhomofarnesic acid amide (I-1) is high, the yield is favorable, and the N,N-dimethylformamide dimethyl acetal (III-1) can be recovered at a high recovery rate, in comparison with the producing methods of the Comparative Examples.

Example 9

N,N-dimethylhomofarnesic acid amide (I-1) was obtained similarly to Example 5 except that xylene was not used and that the reflux ratio was changed to 8. Table 3 illustrates the purity and the yield of the resultant N,N-dimethylhomofarnesic acid amide (I-1), and the recovery rate of the N,N-dimethylformamide dimethyl acetal (III-1) and the decomposition amount thereof.

TABLE 1

|  |  | Comp. Ex. 1 | Ex. 4 | Ex. 3 | Ex. 1 | Ex. 2 | Comp. Ex. 2 |
|---|---|---|---|---|---|---|---|
| Raw material | Nerolidol(II)(mmol) | 57.7 | 57.7 | 57.7 | 57.7 | 57.7 | 57.7 |
|  | DMF-DMA(III-1) (mmol) | 69.2 | 86.6 | 101 | 115.3 | 173.1 | 288.5 |
|  | (molar ratio relative to nerolidol) | 1.2 | 1.5 | 1.75 | 2 | 3 | 5 |
| Result | Solvent | Xylene | Xylene | Xylene | Xylene | Xylene | Xylene |
|  | Yield (%) | 61.1 | 73.8 | 74.2 | 82.0 | 81.1 | 82.2 |
|  | Purity (%) | 61.9 | 77.1 | 81.2 | 83.9 | 83.8 | 84.6 |
|  | Amount of charged DMF-DMA (mol %) | 120.0 | 150.0 | 175.0 | 200.0 | 300.0 | 500.0 |
|  | Amount of reacted DMF-DMA (mol %) | 61.1 | 73.8 | 74.2 | 82.0 | 81.1 | 82.2 |
|  | Amount of recovered DMF-DMA (mol %) | 9.4 | 38.4 | 66.8 | 81.0 | 162.9 | 195.1 |
|  | Recovery rate of raw material DMF-DMA (%) | 58.8 | 74.8 | 80.6 | 81.5 | 81.3 | 55.5 |
|  | Decomposition amount of raw material DMF-DMA (mol %) | 49.5 | 37.8 | 34.0 | 37.0 | 52.0 | 222.7 |

*Ex. and Comp. Ex. indicate Example and Comparative Example respectively.
In Table 1, DMF-DMA indicates N,N-dimethylformamide dimethyl acetal.

Examples 5-8 and Comparative Examples 3-4

N,N-dimethylhomofarnesic acid amide (I-1) was obtained similarly to Example 1 except that xylene was not used and that the amount (in terms of pure content) of N,N-dimethylformamide dimethyl acetal (III-1) was changed as illustrated in Table 2. Table 2 illustrates the purity and the yield of the resultant N,N-dimethylhomofarnesic acid amide (I-1), the recovery rate of N,N-dimethylformamide dimethyl acetal (III-1), and the decomposition amount of N,N-dimethylformamide dimethyl acetal.

TABLE 3

|  |  | Example 5 | Example 9 |
|---|---|---|---|
| Raw material | Nerolidol(II) (mmol) | 57.7 | 57.7 |
|  | DMF-DMA(III-1)(mmol) | 115.3 | 115.3 |
|  | (molar ratio relative to nerolidol) | 2 | 2 |
|  | Reflux ratio | 10 | 8 |
| Result | Solvent | none | none |
|  | Yield (%) | 83.0 | 78.2 |
|  | Purity (%) | 86.0 | 83.4 |

TABLE 2

|  |  | Comp. Ex. 3 | Ex. 8 | Ex. 7 | Ex. 5 | Ex. 6 | Comp. Ex. 4 |
|---|---|---|---|---|---|---|---|
| Raw material | Nerolidol(II)(mmol) | 57.7 | 57.7 | 57.7 | 57.7 | 57.7 | 57.7 |
|  | DMF-DMA(III-1) (mmol) | 69.2 | 86.6 | 101 | 115.3 | 173.1 | 288.5 |
|  | (molar ratio relative to nerolidol) | 1.2 | 1.5 | 1.75 | 2 | 3 | 5 |
| Result | Solvent | none | none | none | none | none | none |
|  | Yield (%) | 62.2 | 71.5 | 74.9 | 83.0 | 81.8 | 82.3 |
|  | Purity (%) | 62.5 | 78.0 | 81.5 | 86.0 | 84.9 | 85.4 |
|  | Amount of charged DMF-DMA (mol %) | 120.0 | 150.0 | 175.0 | 200.0 | 300.0 | 500.0 |
|  | Amount of reacted DMF-DMA (mol %) | 55.1 | 74.0 | 74.9 | 83.0 | 81.8 | 82.3 |
|  | Amount of recovered DMF-DMA (mol %) | 8.9 | 40.3 | 65.2 | 82.0 | 163.5 | 200.3 |
|  | Recovery rate of raw material DMF-DMA (%) | 53.3 | 76.2 | 80.1 | 82.5 | 81.8 | 56.5 |
|  | Decomposition amount of raw material DMF-DMA (mol %) | 56.0 | 35.7 | 34.9 | 35.0 | 54.7 | 217.4 |

*Ex. and Comp. Ex. indicate Example and Comparative Example respectively.
In Table 2, DMF-DMA indicates N,N-dimethylformamide dimethyl acetal.

TABLE 3-continued

|  | Example 5 | Example 9 |
| --- | --- | --- |
| Amount of charged DMF-DMA (mol %) | 200.0 | 200.0 |
| Amount of reacted DMF-DMA (mol %) | 83.0 | 78.2 |
| Amount of recovered DMF-DMA (mol %) | 82.0 | 85.6 |
| Recovery rate of raw material DMF-DMA (%) | 82.5 | 81.9 |
| Decomposition amount of DMF-DMA (mol %) | 35.0 | 36.2 |

Example 10

Production of (±)-Ambroxan (±)-Ambroxan (VI) was produced in accordance with the following Scheme by using N,N-dimethylhomofarnesic acid amide (I-1) as a starting material.

Scheme

[Chemical formula 15]

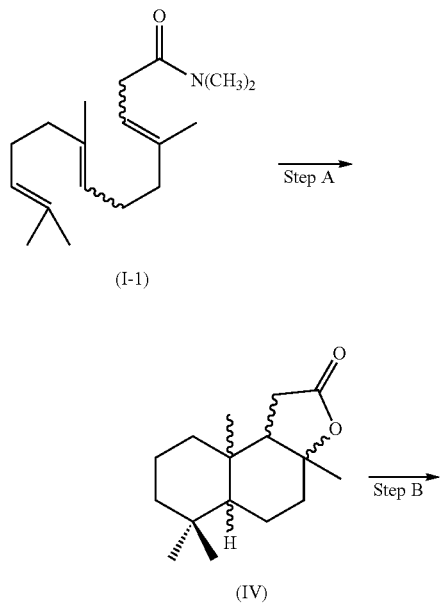

(Step A)

[Chemical formula 16]

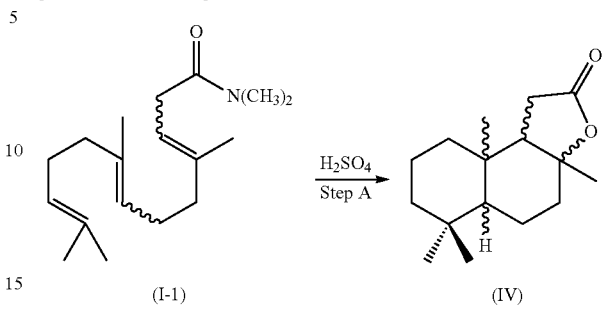

Into a mixed liquid of 733.3 g of concentrated sulfuric acid (7.0 kmol, 3.0 mol times relative to N,N-dialkylhomofarnesic acid amide (I)) and 6.7 kg of dichloromethane, which was cooled to 0° C., a 10 mass % dichloromethane solution of N,N-dimethylhomofarnesic acid amide (I-1) containing 770.8 g of N,N-dimethylhomofarnesic acid amide (I-1) (purity: 83.9%, 2.3 kmol) obtained in Example 1 was dropped in 2 hours. After adding 3.3 kg of water, the mixed liquid was stirred at 25° C. for 50 hours. The aqueous layer of the resultant mixed liquid was neutralized with an aqueous solution of sodium hydroxide, and then, the organic layers were separated, and furthermore, the aqueous layer was extracted twice with 3.3 kg of dichloromethane. The combined organic layer was washed with saturated saline, and then it was dried and from which the solvent was evaporated, so that 694 g of an orange-colored solid was obtained. Analytical results showed that this solid included 345 g in total of diastereomer mixture of (±)-Sclareolide (IV) (yield: 60%, diastereofacial selectivity of (±)-Sclareolide: 41%).

(Step B)

[Chemical formula 17]

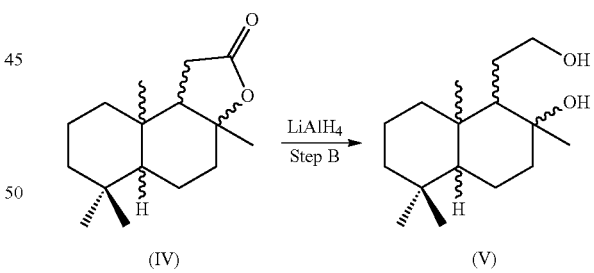

A suspension prepared by dispersing 73.3 g (1.9 mol) of lithium aluminum hydride in 2.6 kg of absolute diethyl ether was cooled to 0° C. A solution prepared by dissolving, in 2.6 kg of absolute diethyl ether, 479 g of solid including 238.3 g (0.9 mol) of diastereomer mixture of (±)-Sclareolide (IV) obtained in Step A was dropped into the suspension in 15 minutes. After completion of the dropping, the mixture was stirred further under a reflux for 1 hour. After cooling to room temperature, 3.9 kg of an aqueous solution of 10 mass % sodium hydroxide was dropped into the mixture, and the separated aqueous layer was extracted twice with 2.6 kg of diethyl ether. The combined organic layer was washed with a saturated aqueous solution of ammonium chloride, and then it was dried and from which the solvent was evaporated, so that 738 g of a light-yellow semi-solid was obtained. Analytical results showed that this semi-solid included 219 g in total of diastereomer mixture of (±)-Ambroxdiol (V) (yield: 90%).

(Step C)

[Chemical formula 18]

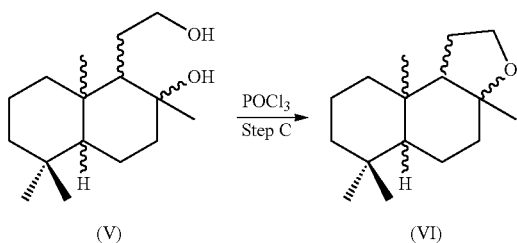

A solution was prepared by dissolving 711 g of a semi-solid including 210.0 g (0.8 mol) of diastereomer mixture of (±)-Ambroxdiol (V) in 6.0 kg of anhydrous pyridine cooled to 0° C. Into this solution, 156.0 g (1.0 mol) of phosphorus oxychloride was dropped in 5 minutes and then stirred for 2 hours. Subsequently, 3.0 kg of 10 mass % aqueous solution of sodium hydroxide was dropped into the mixture at 0° C., and the separated aqueous layer was extracted twice with 3.0 kg of diethyl ether. The combined organic layer was washed with a saturated aqueous solution of ammonium chloride, and then it was dried and from which the solvent was evaporated, so that 651 g of diastereomer mixture of oil-like rude (±)-Ambroxan (VI) was obtained. Analytical results showed that this diastereomer mixture of rude (±)-Ambroxan (VI) included in total 126 g of (±)-Ambroxan (VI) (yield: 65%), and the diastereo purity of the (±)-Ambroxan (VI) was 44%. The resultant (±)-Ambroxan had a strong amber-like aroma.

INDUSTRIAL APPLICABILITY

N,N-dialkylhomofarnesic acid amide (I) obtained by the producing method of the present invention can be used favorably as a precursor of (±)-Ambroxan (VI) that is an important material of an amber-like fragrance having an excellent aroma property and fragrance retention. Further, according to the method of the present invention, since the yield and the purity of N,N-dialkylhomofarnesic acid amide (I) and also the recovery rate of the raw material (N,N-dialkylformamide dimethyl acetal (II)) are high, the above-mentioned N,N-dialkylhomofarnesic acid amide (I) of a high purity can be produced efficiently.

The invention claimed is:

1. A method for producing N,N-dialkylhomofarnesic acid amide by reacting nerolidol with N,N-dialkylformamide dimethyl acetal under the condition that the N,N-dialkylformamide dimethyl acetal can be refluxed,
wherein the molar ratio of the N,N-dialkylformamide dimethyl acetal to the nerolidol is in a range of 1.5 to 3.

2. The method for producing N,N-dialkylhomofarnesic acid amide according to claim 1, wherein the reaction is conducted under the conditions that the N,N-dialkylformamide dimethyl acetal can be refluxed in a case where no organic solvent is contained or an organic solvent is contained in an amount of less than 100 mass % relative to the nerolidol.

3. The method for producing N,N-dialkylhomofarnesic acid amide according to claim 2, wherein the organic solvent is a hydrocarbon.

4. The method for producing N,N-dialkylhomofarnesic acid amide according to claim 1, wherein the molar ratio of the N,N-dialkylformamide dimethyl acetal to the nerolidol is in a range of 2 to 3.

5. The method for producing N,N-dialkylhomofarnesic acid amide according to claim 1, wherein the reflux is conducted using a rectifier.

6. The method for producing N,N-dialkylhomofarnesic acid amide according to claim 5, wherein the number of plates of the rectifier is 3 or more.

7. The method for producing N,N-dialkylhomofarnesic acid amide according to claim 5, wherein the number of plates of the rectifier is 40 or less.

8. The method for producing N,N-dialkylhomofarnesic acid amide according to claim 1, wherein the reflux is conducted under the conditions that the reflux ratio is 3 or more.

9. The method for producing N,N-dialkylhomofarnesic acid amide according to claim 1, wherein the reflux is conducted under the conditions that the reflux ratio is 5 or more and 40 or less.

10. The method for producing N,N-dialkylhomofarnesic acid amide according to claim 1, wherein the condition that the N,N-dialkylformamide dimethyl acetal is refluxed is that the temperature is equal to or higher than the boiling point of the N,N-dialkylformamide dimethyl acetal (III) under the conditions of a pressure of 101 kPa.

11. The method for producing N,N-dialkylhomofarnesic acid amide according to claim 1, wherein the molar ratio of the N,N-dialkylformamide dimethyl acetal to the nerolidol is in a range of 2 to 2.5.

12. The method for producing N,N-dialkylhomofarnesic acid amide according to claim 1, wherein the reflux is conducted under the conditions that the reflux ratio is 8 or more and 15 or less.

13. A method for producing (±)-3a,6,6,9a-tetramethyldodecahydronaphtho[2.1-b]furan, comprising Steps 1-4 below:
Step 1: reacting nerolidol with N,N-dialkylformamide dimethyl acetal under the conditions that the N,N-dialkylformamide dimethyl acetal can be refluxed to produce N,N-dialkylhomofarnesic acid amide, wherein the molar ratio of the N,N-dialkylformamide dimethyl acetal to the nerolidol is in a range of 1.5 to 3;
Step 2: cyclizing the N,N-dialkylhomofarnesic acid amide obtained in Step 1 in the presence of an acidic agent and further hydrolyzing to obtain Sclareolide;
Step 3: reducing the Sclareolide obtained in Step 2 so as to obtain Ambroxdiol; and
Step 4: dehydrating and cyclizing the Ambroxdiol obtained in Step 3 so as to obtain (±)-3a,6,6,9a-tetramethyldodecahydronaphtho[2.1-b]furan.

14. The method for producing (±)-3a,6,6,9a-tetramethyl-dodecahydronaphtho[2.1-b]furan according to claim 13, wherein the acidic agent is one or more of Brönsted acid and Lewis acid selected from the group consisting of sulfuric acid, methanesulfonic acid, paratoluenesulfonic acid, chlorosulfonic acid, trifluoromethane sulfonic acid, a metal chloride and a boron trifluoride ether complex.

15. The method for producing (±)-3a,6,6,9a-tetramethyl-dodecahydronaphtho[2.1-b]furan according to claim 13, wherein the acidic agent is used in an amount of 0.1 to 10 mol times relative to the N,N-dialkylhomofarnesic acid amide (I).

16. The method for producing (±)-3a,6,6,9a-tetramethyl-dodecahydronaphtho[2.1-b]furan according to claim 13, wherein a solvent is used further in an amount of 1 to 100 mass times relative to the N,N-dialkylhomofarnesic acid amide (I) in Step 2.

17. The method for producing (±)-3a,6,6,9a-tetramethyl-dodecahydronaphtho[2.1-b]furan according to claim 16, wherein the solvent is a hydrocarbon, a halogenated hydrocarbon, a nitrohydrocarbon, or an ether.

18. The method for producing (±)-3a,6,6,9a-tetramethyl-dodecahydronaphtho[2.1-b]furan according to claim 13, wherein the cyclization reaction in Step 2 is conducted at a temperature in a range of −70° C. to 100° C.

19. The method for producing (±)-3a,6,6,9a-tetramethyl-dodecahydronaphtho[2.1-b]furan according to claim 13, wherein the reduction in Step 3 is conducted in the presence of a reducer.

20. The method for producing (±)-3a,6,6,9a-tetramethyl-dodecahydronaphtho[2.1-b]furan according to claim 13, wherein the dehydration-cyclization in Step 4 is conducted by using a dehydrating agent.

\* \* \* \* \*